United States Patent
Laurin et al.

(10) Patent No.: US 12,312,305 B2
(45) Date of Patent: May 27, 2025

(54) PRODUCTION OF HEAVY ISOPARAFFINIC HYDROCARBONS

(71) Applicant: LUMMUS TECHNOLOGY LLC, Houston, TX (US)

(72) Inventors: Marc Andrew Laurin, Houston, TX (US); Rosette Barias, Houston, TX (US); Manoj Som, Houston, TX (US); Liang Chen, Houston, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 129 days.

(21) Appl. No.: 18/314,617

(22) Filed: May 9, 2023

(65) Prior Publication Data

US 2023/0365478 A1    Nov. 16, 2023

Related U.S. Application Data

(60) Provisional application No. 63/364,600, filed on May 12, 2022.

(51) Int. Cl.
  *C07C 5/03*    (2006.01)
  *B01J 8/02*    (2006.01)
  (Continued)

(52) U.S. Cl.
  CPC .............. *C07C 5/03* (2013.01); *B01J 8/0242* (2013.01); *B01J 8/0278* (2013.01); *B01J 8/0285* (2013.01);
  (Continued)

(58) Field of Classification Search
  None
  See application file for complete search history.

(56) References Cited

U.S. PATENT DOCUMENTS

| 5,431,888 A | * | 7/1995 | Hickey | ............... C07C 41/06 203/DIG. 6 |
| 9,315,737 B2 | | 4/2016 | Dupassieux et al. | |

(Continued)

FOREIGN PATENT DOCUMENTS

| CN | 101880549 A | 11/2010 |
| CN | 102533306 A | 7/2012 |

(Continued)

OTHER PUBLICATIONS

International Search Report issued in Application No. PCT/US2023/021720, mailed on Sep. 1, 2023 (4 pages).

(Continued)

*Primary Examiner* — Tam M Nguyen
(74) *Attorney, Agent, or Firm* — Osha Bergman Watanabe & Burton LLP

(57) ABSTRACT

Processes and systems for the production of heavy isoparaffinic hydrocarbons include feeding hydrogen and a mixed isoolefin stream, including C8-C12 olefins, isoolefins, and oligomers, and C8-C12+ hydrogenated hydrocarbons to a trickle-bed reactor system. The hydrogen and mixed isoolefin are reacted over a hydrogenation catalyst, producing a liquid effluent comprising hydrogenated hydrocarbons and unreacted olefins and oligomers, and a vapor effluent comprising hydrogenated hydrocarbons, hydrogen and unreacted olefins and oligomers. The liquid effluent is fed to a first heat exchanger, producing a cooled liquid effluent stream, which is combined with the vapor effluent, producing a mixed phase effluent. The mixed phase effluent is cooled in a second heat exchanger, producing a partially condensed effluent, which is fed to a drum, producing a vent stream, a hydrogenated product stream having greater than 95 wt % C8-C12 saturated hydrocarbons, and a hydroge- (Continued)

nated recycle stream. The hydrogenated product stream may be provided to downstream blending systems.

11 Claims, 3 Drawing Sheets

(51) Int. Cl.
*C07C 5/08* (2006.01)
*C07C 5/09* (2006.01)

(52) U.S. Cl.
CPC . *B01J 2208/00849* (2013.01); *C07C 2523/42* (2013.01); *C07C 2523/44* (2013.01); *C07C 2523/745* (2013.01); *C07C 2523/755* (2013.01)

(56) References Cited

U.S. PATENT DOCUMENTS

| | | |
|---|---|---|
| 2011/0024327 A1 | 2/2011 | Marker et al. |
| 2012/0165581 A1 | 6/2012 | Dupassieux et al. |
| 2014/0163272 A1* | 6/2014 | Mukherjee ............. C10G 45/00 585/254 |
| 2015/0152336 A1* | 6/2015 | Greene ................... C10G 65/04 422/162 |
| 2019/0119184 A1 | 4/2019 | Ohler et al. |

FOREIGN PATENT DOCUMENTS

| | | |
|---|---|---|
| RU | 2606629 C2 | 1/2017 |
| WO | 2013/095766 A1 | 6/2013 |

OTHER PUBLICATIONS

Written Opinion issued in Application No. PCT/US2023/021720, mailed on Sep. 1, 2023 (6 pages).

Office Action issued in corresponding EA Application No. 202492353 dated Mar. 17, 2025 (3 pages).

* cited by examiner

PRODUCTION OF HEAVY ISOPARAFFINIC HYDROCARBONS

FIELD OF THE DISCLOSURE

Embodiments disclosed herein relate generally to a process for the hydrogenation of an olefinic stream. Some embodiments herein relate to processes and apparatus for the hydrogenation of isoolefins, such as isooctene or diisoamylene, at high conversion.

BACKGROUND

In order to meet the fuel blending requirements, such as octane rating or vapor pressure requirements, smaller molecules may be upgraded to produce longer chain hydrogenated molecules.

One commonly used method of upgrading smaller olefin molecules, such as $C_2$ to $C_5$ olefins, is a dimerization, trimerization, or oligomerization reaction. Isobutylene and isoamylene are commercially significant in many applications. For example, isobutylene is one of the comonomers in butyl rubber. Isobutylene can also be dimerized to produce compounds that can be used as chemical feedstock for further reacting or in gasoline blending.

Dimerization reactions involve contacting an olefin with a catalyst in order to produce a longer chain molecule. An oligomer can consist of two or more constituent olefin molecules. For example, dimerization is a type of oligomerization reaction that is limited to a combination of only two olefin molecules. If the olefin feed contains only one type of olefin, a dimer product is formed. If the olefin feed contains two or more different olefins or olefin isomers, a codimer product may also be formed.

Specifically, $C_4$ olefin dimerization is widely used for producing isooctene, an intermediate that can be hydrogenated to produce isooctane, a high-value gasoline blending additive. Similarly, isoamylene can be dimerized to produce diisoamylene. In either process, a small amount of trimer may also be formed due to a secondary trimerization reaction, resulting in a C12+ olefin product stream.

In some cases, it is desired to hydrogenate the dimerized product to produce a hydrogenated C8-C12+ stream for product blending.

Prior art hydrogenation processes are applicable only to the specific feedstock for which they have been designed. The catalyst and the operating conditions for a given hydrogenation process are generally tailored to a specific, limited feedstock, and differ significantly across feedstocks, meaning that processes for the hydrogenation of heavy naphtha cannot be readily used for converting light naphtha.

Hydrogenation processes which have been developed for pure feed components, often cannot be used for processing distillate fractions containing mixtures of various isomers and length of olefinic hydrocarbons. This is partly because the varied reactivity of different hydrocarbons, including the differences in the exotherm for C8s, C10s and C12s. This means in practice that, under the reaction conditions suitable for complete hydrogenation of a C8 olefin, considerable amounts of the heavier olefinic compounds will remain unsaturated.

Accordingly, most production facilities are designed to separate oligomerization products into a number of hydrocarbon streams to be used as light and heavy fuels and solvents as well as raw material for petrochemical processes. These streams are then individually hydrogenated using a number of different hydrogenation units tailored to each specific feed. Using a single unit designed for flexible hydrogenation of different feeds would lead to poor conversion, catalyst, energy, and raw material consumption, poor product quality and so forth.

Accordingly, there exists a continuing need for improved isoolefin hydrogenation systems and processes.

SUMMARY OF THE DISCLOSURE

One or more embodiments disclosed herein relate to a process for the hydrogenation of isoolefins. The process may include feeding hydrogenated hydrocarbons and a mixed isoolefin stream, including C4 to C12+ isoolefins, such as C4 to C8 or C8 to C12 olefins and oligomers (dimers, trimers, tetramers), and/or C5 to C15+ isoolefins, such as C5 to C10 of C10 to C15 olefins and oligomers, to a trickle-bed reactor system containing one or more beds of a hydrogenation catalyst, and feeding a hydrogen feed stream to the trickle-bed reactor system. In some embodiments, the process may include feeding C8-C12 isoolefins, C8-C12 diisoolefins, and C8-C12 hydrogenated hydrocarbons, to a trickle-bed reactor system containing one or more beds of a hydrogenation catalyst, and feeding a hydrogen feed stream to the trickle-bed reactor system. In other embodiments, the process may include feeding C10-C15 isoolefins, C10-C15 diisoolefins, and C10-C15 hydrogenated hydrocarbons, to a trickle-bed reactor system containing one or more beds of a hydrogenation catalyst, and feeding a hydrogen feed stream to the trickle-bed reactor system. The hydrogen feed stream and the mixed isoolefin stream are reacted in the presence of the one or more beds of hydrogenation catalyst, producing a liquid effluent comprising hydrogenated hydrocarbons and unreacted olefins and a vapor effluent comprising hydrogenated hydrocarbons, hydrogen, and unreacted olefins. The liquid effluent is fed to a first heat exchanger, cooling the liquid effluent, and producing a cooled liquid effluent stream, which is combined with the vapor effluent, producing a mixed phase effluent. The mixed phase effluent is fed to a second heat exchanger, cooling the mixed phase effluent, and producing a partially condensed effluent, which is fed to a drum, producing a vent stream, a hydrogenated product stream comprising greater than 95 wt % saturated hydrocarbons, such as C8-C15, C8-C12, or C10-C15 hydrocarbons, and a hydrogenated recycle stream. The process further includes recovering the hydrogenated product stream and sending the hydrogenated product stream to one or more downstream blending systems.

According to one or more embodiments disclosed herein is a system for the hydrogenation of isoolefins. The system includes a trickle-bed reactor system comprising one or more beds of a hydrogenation catalyst. The trickle-bed reactor system is configured for concurrently: receiving a mixed isoolefin stream, comprising C8-C15 isoolefins, as described above, such as C8-C12+ olefin dimers, trimers, and tetramers, and C8-C15 hydrogenated hydrocarbons, as described above; receiving a hydrogen feed stream; reacting the hydrogen feed stream and the mixed isoolefin stream in the presence of one or more beds of hydrogenation catalyst; and, producing a liquid effluent comprising hydrogenated hydrocarbons and unreacted olefins and a vapor effluent comprising hydrogenated hydrocarbons, hydrogen, and unreacted olefins. The system further includes a first feed line for transporting the liquid effluent to a first heat exchanger, which is configured for cooling the liquid effluent, producing a cooled liquid effluent stream. The system also includes a second feed line for transporting the vapor effluent and combining the vapor effluent with the cooled liquid effluent, producing a mixed phase effluent. A second heat exchanger is provided, configured for receiving the mixed phase effluent and cooling the mixed phase effluent, producing a partially condensed effluent. A third feed line is also provided for transporting the partially condensed effluent to a drum. The drum includes: an overhead vent configured for producing a vent stream comprising hydrogen; a hydrogenated product outline configured for producing a hydrogenated product stream comprising greater than 95 wt % C8-C12+ hydrogenated hydrocarbons and, a hydrogenated recycle stream outlet configured for producing a hydrogenated recycle stream. A flow conduit is also provided for sending the hydrogenated product stream to one or more downstream blending systems.

According to one or more embodiments disclosed herein is a process for the hydrogenation of isoolefins. The process may include feeding a mixed isoolefin stream, including C8-C15 isoolefins, as described above, such as C8-C12+ olefin dimers, trimers, and tetramers, and C8-C15 hydrogenated hydrocarbons, as described above, to a trickle-bed reactor system containing one or more beds of a hydrogenation catalyst. A hydrogen feed stream is also fed to the trickle-bed reactor system. The process also includes reacting the hydrogen feed stream and the mixed isoolefin stream in the presence of the one or more beds of hydrogenation catalyst, producing a liquid effluent comprising hydrogenated hydrocarbons and unreacted olefins and a vapor effluent comprising hydrogenated hydrocarbons, hydrogen, and unreacted olefins. The liquid effluent is fed to a first heat exchanger, cooling the liquid effluent, and producing a cooled liquid effluent stream, which is combined with the vapor effluent, producing a mixed phase effluent. The mixed phase effluent is fed to a second heat exchanger, cooling the mixed phase effluent, and producing a partially condensed effluent, which is fed to a drum, producing a vent stream, a hydrogenated product stream comprising greater than 95 wt % C8-C12+ saturated hydrocarbons, and a hydrogenated recycle stream. The process further includes recovering the hydrogenated product stream and sending the hydrogenated product stream to one or more downstream blending systems. The hydrogenated recycle stream is pressurized in a pump, producing a pressurized recycle stream, which is fed to the first heat exchanger. In the first heat exchanger, the pressurized recycled stream and cool the liquid effluent are heated, producing an intermediate recycle stream. The process also includes heating the intermediate recycle stream in a third heat exchanger, producing a heated recycle stream, combining the heated recycle stream with a fresh isoolefin stream comprising C8-C12 isoolefins and C8-C12 diisoolefins, and producing the mixed isoolefin stream, wherein the heated recycle stream and the fresh isoolefin stream may be fed to the trickle-bed reactor at a volume ratio of 3:1 to 10:1.

Other aspects and advantages will be apparent from the following description and the appended claims.

DETAILED DESCRIPTION

Figure 1:
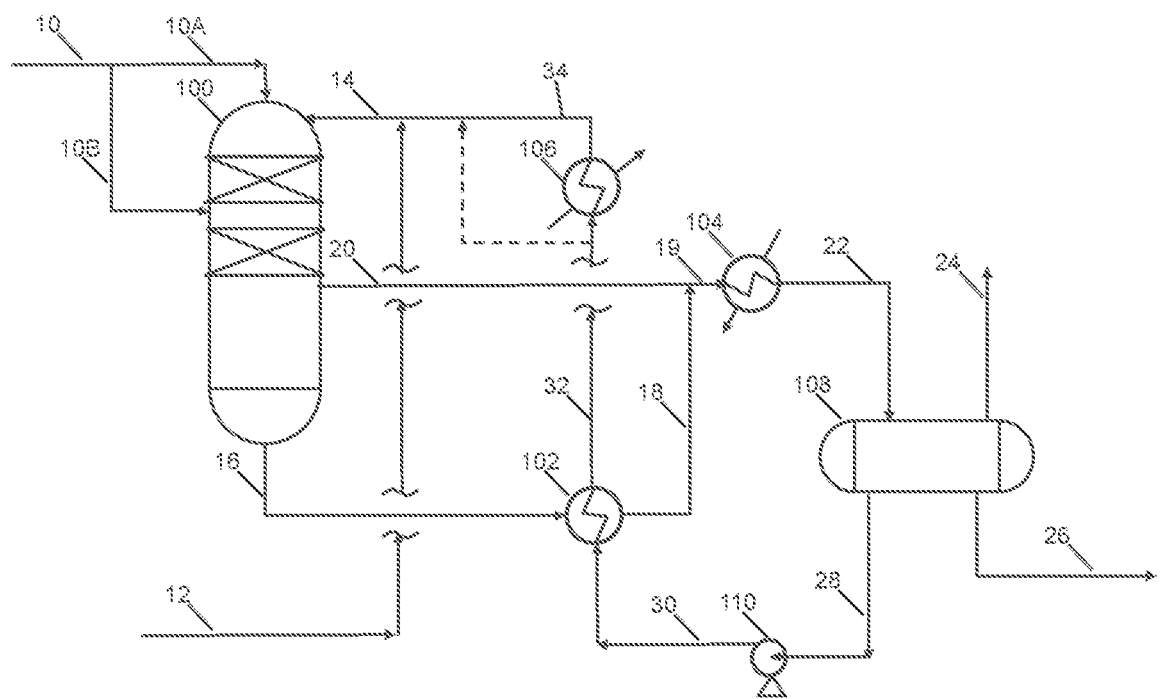
FIG. 1 is a simplified process flow diagram of a system for hydrogenation of isoolefin mixtures according to embodiments herein.

For the purpose of this description, a single reference number will be assigned to a line as well as a stream carried in that line. Same reference numbers refer to similar components. The person skilled in the art will readily understand that, while this disclosure is illustrated making reference to one or more specific combinations of features and measures, many of those features and measures are functionally independent from other features and measures such that they can be equally or similarly applied independently in other embodiments or combinations.

Embodiments herein relate generally to hydrogenation of isoolefins. In some embodiments, the processes and system relate generally to total hydrogenation of a mixed diisoolefin stream. Such hydrogenation processes may require the control of the exothermic reactions brought about by the type of olefins contained in the feed mixture. The exothermic reaction can vary greatly with C8s, C10s, C12+ olefins. In view of the above, known processes would require the separation of the heavy olefins and subsequent hydrogenation of each type of olefin separately in order to control the temperature to avoid undesirable side reactions or product degradation.

Reactors useful in embodiments disclosed herein may include traditional fixed bed reactors, boiling point reactors, trickle-bed reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions involving hydrogenation of isoolefin mixtures according to embodiments herein may include tubular fixed bed reactors, bubble column reactors, slurry reactors, pulsed flow reactors, down-flow reactors, trickle-bed reactors, or any combination of these reactors. Multiple reactor systems useful in embodiments disclosed herein may include a series of multiple reactors or multiple reactors in parallel for the first reaction zone. A person of ordinary skill in the art would recognize that other types of reactors may also be used.

The reactors useful in embodiments disclosed herein may include any physical devices or a combination of two or more devices, including reactors and reactor systems as described above. The reactor(s) may have various internal devices for mixing the vapor and liquid components. Reaction zones within the reactor(s) may include "wettable" structure and/or packing. Wettable structure and packing useful in embodiments disclosed herein may include various packing materials, which may be catalytic or non-catalytic. Suitable wettable structure and packing may include, for example, random or dumped packings which are: catalytically inert dumped packings that contain higher void fraction and maintain a relatively large surface area, such as, Berl Saddles (Ceramic), Raschig Rings (Ceramic), Raschig Rings (Steel), Pall rings (Metal), Pall rings (Plastic, e.g. polypropylene) and the like. Monoliths, which are structures containing multiple, independent, vertical channels and may be constructed of various materials such as plastic, ceramic, or metals, in which the channels are typically square, are also suitable wettable structures. Other geometries could also be used.

Other materials that promote the distribution of liquid may also be used, including mist eliminators, demisters, or other wire or multi-filament type structure. Such multi-filament structures may include one or more of fiberglass, steel, Teflon, polypropylene, polyethylene, polyvinylidene difluoride (PVDF), polyester, or other various materials, which may be knitted (or co-knit, where more than one type of filament or wire structure is used), woven, non-woven, or any other type of multi-filament structure. Structures including multifilament wires as typically used in demister services, structures including an element of woven fiberglass cloth, and high surface area stainless steel structured packings are preferred.

Reactors according to embodiments disclosed herein may include one or multiple reaction zones and one or multiple beds of catalytic material.

The hydrocarbon feed to the reactor(s), according to one or more embodiments herein, may include mixed olefinic streams, such as a feed stream containing dimers of isobutylene or isoamylenes, codimers of isobutylene and isoamylene, or mixtures thereof. One of the primary products from processes according to embodiments herein may include hydrogenated products of a mixed diisoolefin stream from a dimerization process. For example, isobutylene may be dimerized to form a C8 tertiary olefin and subsequently hydrogenated to form C8 paraffins. In some embodiments, the dimers have 8 to 15+ carbon atoms, such as 8 to 12 or 10 to 15 carbon atoms, and correspond to dimers prepared from dimerization or oligomerization of C4, C5, or heavier olefins.

Hydrogenations is a process comprising the steps of feeding a hydrocarbon stream into a hydrogenation unit, contacting said hydrocarbon stream with hydrogen in the presence of a catalyst in order to hydrogenate the olefinic compounds contained therein to produce a saturated product or paraffin, and recovering the saturated product from the hydrogenation unit. In general, the goal may be to saturate all double bonds present, known as total hydrogenation. However, one of ordinary skill may recognized that sufficient conversion may be between 80 and 99.9% of olefinic compounds in the hydrocarbon stream. Conversion may be dependent on the process conditions (temperature, pressure, space velocity), hydrogen flow rate, catalyst type, catalyst age, etc.

Overall conversion may also be dependent on the hydrogenation process choices. In the present case, when the process is conducted through the down-flow trickle-bed reactor, the conversion within the one or more catalyst zones may be from 80 to 95%, where at least a part of the olefinic compounds are hydrogenated. The remaining olefinic compounds are further hydrogenated in a lower catalyst bed, or as part of a recycle, or both, leading to a desired overall conversion, such as from 95 to 99.9%.

In prior olefin hydrogenation processes, the mixed olefinic stream must be separated into discrete hydrocarbon fractions, such as a C8 stream, a C10 stream, and a C12 stream, for example, and each fraction recovered is separately hydrogenated. This is conventionally required in order to control the exothermic reaction, avoid catalyst degradation, and produce a consistent, quality product. The present inventors have found that through proper conditions and appropriate use of heat exchanger and recycle, the need for an upstream separation system can be eliminated while still achieving a high conversion.

Operating conditions within trickle-bed reactor systems for hydrogenation of mixed diisoolefins may include temperatures and pressures sufficient for complete hydrogenation of C8-C12 diisoolefins, C8-C15 diisoolefins, or C10-C15 diisoolefins. The temperature within the reaction zone may thus be intimately linked to the pressure, the combination of which provides for boiling of the diisoolefins, thus keeping the non-hydrogenated components in contact with the one or more catalyst beds.

Typical conditions for the hydrogenation reaction include catalyst bed temperatures of about 50-300° C., hydrogen partial pressure of about 5-75 barg in some embodiments, 20-40 barg in other embodiments, or 28-35 in other embodiments, and equivalent liquid hourly space velocities of about 1.0 to 2.0 $hr^{-1}$. The temperature in the column is determined by the inlet temperature of the liquid feed. The temperature of the liquid feed may be controlled to a temperature between 30-100° C. through the use of a hydrogenated recycle stream; for example, embodiments herein may include heating the intermediate recycle stream in the third heat exchanger to a temperature sufficient to heat the mixed isoolefin stream to a temperature in the range of 30-100° C. Temperature in the column may have a 50-100° C. temperature rise across the reactor during standard operating conditions, and may be further controlled by a high recycle flowrate to avoid increasingly higher temperatures. Even though a trickle-bed reactor is used, some of the isoolefins may be unconverted and may exit the column with the bottoms.

The hydrogenated product is removed from the trickle-bed reactor as a bottoms, along with a small amount of unconverted olefins. A middle cut vapor stream of hydrogenated product and unconverted olefins may be withdrawn below the bottom of the one or more catalyst beds. The middle cut vapor stream may also contain hydrogen and light hydrocarbons which have been vaporized during the hydrogenation reaction. Such middle cut may be used to control the exothermic reaction thereby producing a stable, hydrogenated reaction product from the mixed olefinic feedstock.

A number of hydrogenation catalysts are known in the art. The catalysts may be provided on an oxide support. The catalyst can vary in shape and may be spheres or extruded cylinders or lobed shapes. Known hydrogenation catalysts typically comprise a metal selected from platinum, palladium, iron, and nickel.

For hydrogenation reactions in the one or more catalyst zones, hydrogen is provided in excess, typically from 1.05 times to 10 times the stoichiometrically required amount for complete hydrogenation of the olefins in the feed stream; from 1.5 to 10 times the stoichiometrically required amount in other embodiments. Hydrogen feeds may include fresh hydrogen and recycled hydrogen. Fresh hydrogen may be supplied from a dedicated hydrogen generation unit. Recycled hydrogen may be obtained from a number of known hydrogen recycle systems. Additionally, the hydrogen may be fed to the hydrogenation reaction system in a number of different locations depending the configuration, desired conversion, and diluent flow rate.

Referring now to FIG. 1, a simplified process flow diagram of a system for the hydrogenation of isoolefin mixtures according to embodiments disclosed is illustrated. While described primarily with respect to C4 oligomers, the system may be operated similarly for C5 oligomers or a mixture of C4 and C5 oligomers.

An olefinic hydrocarbon feed, such as a dimerization product stream, including C8-C12+ diisoolefins, may be fed via a flow line 12, to a reactor 100. In one or more embodiments, the olefin hydrocarbon feed may include 80-90 wt % C8 olefins, 10-15 wt % C12 olefins, 0.1-5 wt % C16+ olefins, and, depending upon upstream processing, a trace amount of ethers. The reactor 100 may be a down-flow, liquid-phase, catalytic reaction system, such as a trickle bed reactor, containing one or more beds of hydrogenation catalyst. The olefinic hydrocarbon feed 12 may be combined with a heated, hydrogenated recycle stream 34, forming mixed feed stream 14, and fed to an inlet at the top of the reactor 100.

Fresh or recycled hydrogen may be fed via flow line 10 to reactor 100. The hydrogen stream 10 may be split upstream of reactor 100 into a first hydrogen feed 10A which may be fed to an inlet proximate to the top of the reactor 100. In one or more embodiments where two catalyst zones are located within the reactor 100, the second hydrogen feed 10B may be fed to the reactor 100 at an inlet intermediate the catalyst zones in order to provide additional hydrogen in the lower catalyst bed(s), thereby making up for hydrogen consumed by the hydrogenation process in the upper catalyst bed(s). While described herein generally as two catalyst beds, any number of catalyst beds may be used depending on the feedstock and desired conversion. In one or more embodiments, 1-10 catalyst beds may be used. In one or more embodiments, additional hydrogen may also be fed to an inlet located below the catalyst beds, if necessary, for complete or essentially complete conversion of olefins.

In reactor 100, the diisoolefins react, in the presence of hydrogen and the hydrogenation catalyst contained in the reaction zones, to convert at least a portion of the diisoolefins to paraffins. The components flowing downward through the reaction zones of the liquid-phase trickle bed reactor may then exit the reaction zones into a decant section of the reactor or into a separate decanter, allowing the unreacted hydrogen and any vaporized hydrocarbons or byproducts to be decanted and recovered as a vapor effluent 20, and the remaining liquid products to be recovered as a liquid effluent 16.

The liquid effluent 16 may be withdrawn from the bottom of reactor 100. The liquid effluent may be a substantially hydrogenated product, such as above 80 wt % hydrogenated product in some embodiments, and 95 wt %+ in other embodiments, with some residual olefinic hydrocarbons. The liquid effluent 16 may be fed to a first heat exchanger 102 where the temperature is reduced to 40-120° C. The cooled liquid effluent 18 may then be combined with a vapor effluent 20 from reactor 100, such as in a mixing tee, downstream of the first heat exchanger 102. The vapor effluent 20 may be withdrawn from a side-draw in reactor 100 located below the one or more catalyst beds/at an upper end of the decant zone. The combined vapor/liquid effluent 19 may be fed to a second heat exchanger 104 where the combined vapor/liquid effluent is further cooled to 30-80° C., condensing and/or absorbing hydrocarbons contained in the vapor effluent.

The partially condensed stream 22 may then be fed to a drum 108. The drum 108 may be operated at temperature and pressure suitable to separate the remaining vaporous components into a gaseous fraction and a liquid fraction. In one or more embodiments, the drum may be operated at a temperature from 30 to 80° C. and a pressure from 10 to 40 barg.

The drum 108 may produce a gaseous component stream via vent stream 24, which may consist mostly of hydrogen, a hydrogenated product stream 26, and a hydrocarbon recycle stream 28. The hydrogen in vent stream 24 may optionally be returned to the hydrogen feed 10 as part of the recycled hydrogen.

Hydrogenated product stream 26 may be a substantially hydrogenated product of C8-C12+ paraffins. In one or more embodiments, the hydrogenated product may be 95 wt % paraffins or more, such as at least 98 wt %, 99 wt %, 99.5 wt %, 99.8 wt %, or 99.9 wt % paraffins. In one or more embodiments, the olefins in the product stream 26 may be limited to 5 wt % olefins or less. In one or more embodiments, the olefins in the product stream 26 may be limited to at most 2 wt %, 1 wt %, 0.5 wt %, 0.2 wt %, or 0.1 wt %. Such a product stream may suitable for direct blending in gasoline pools, for example.

The hydrocarbon recycle stream 28 may have a similar composition to product stream 26, and thus in one or more embodiments, may also be removed as additional product with product stream 26. However, in one or more embodiments, the hydrocarbon recycle stream 28 may be used as feed diluent to aid in controlling the exothermic reaction in reactor 100, thereby allowing for the mixed olefinic feed to be hydrogenated without upstream separation. This may be accomplished by pressurizing hydrocarbon recycle stream 28 in a pump 110. The pump 110 may increase the pressure of the stream to 15 to 45 barg, producing a pressurized recycle stream 30. The pressurized recycle stream may be fed to the first heat exchanger 102 (a recycle/effluent exchanger), where the temperature of the pressurized recycle stream 30 is increased to about 40 to 100° C., producing an intermediate recycle stream 32. The intermediate recycle stream 32 may be further heated in a third heat exchanger 106 to produce the heated recycle stream 34 which may be combined with the olefinic hydrocarbon feed 12, such as in a mixing tee, and fed to reactor 100.

Combining the heated recycle stream 34 with the olefinic hydrocarbon feed 12 may be performed for a few reasons. The heated recycle stream 34, being primarily hydrogenated hydrocarbons, may serve as a reaction diluent in reactor 100. In one or more embodiments, the recycle to fresh feed may be at a volume ratio of 3:1 to 10:1, or 4:1 to 8:1, such as about 5:1. The relatively high amount of hydrogenated, recycled, hydrocarbon may aid in controlling the exothermic reaction within the reactor 100, controlling the vaporization and temperature rise within the reactor, thereby preventing a run-away reaction where the olefins undergo additional oligomerization, producing larger hydrocarbons.

Additionally, through the use of the first heat exchanger 102 and third heat exchanger 106, the temperature of the recycle stream may be raised to a point where, by direct mixing with olefinic hydrocarbon feed 12, the temperature of the mixed feed stream 14 may be raised by 10-20° C. above the olefinic hydrocarbon feed 12 temperature. This may ensure that the olefinic feed is hot enough to initiate hydrogenation, while not being hot enough to cause a run-away reaction within reactor 100. For example, the first heat exchanger 102 and third heat exchanger 106 may be configured to heat the hydrogenated recycle stream to a temperature which may be high enough that, after mixing with the olefinic hydrocarbon feed 12, the mixed hydrocarbon feed 14 is at a feed temperature of 30-100° C. in one or more embodiments, or at a feed temperature of 45-80° C. in other embodiments.

As noted above, the exothermic reaction may result in a temperature increase of 60 to 70° C., for example. In one more embodiments, the liquid effluent 16 may be at a temperature sufficiently high enough to heat the pressurized recycle stream 30 to the necessary temperature to ensure the mixed hydrocarbon feed 14 is at the desired feed temperature. In such embodiments, the third heat exchanger 106 may be configured with a bypass, thereby avoiding excess heating of the feed stream. Accordingly, the third heat exchanger 106 may be used primarily during start-up operations when additional heating is required, or during operating conditions where a lesser or greater amount of diluent hydrocarbon is required.

In one or more embodiments, a first portion of the intermediate recycle stream 32 may bypass the third heat exchanger 106 while a second portion of the intermediate recycle stream 32 is passed through the third heat exchanger 106. In this fashion, the final temperature of mixed hydrocarbon feed 14 may be controlled. In one or more embodiments, the third heat exchanger 106 may only be used during start up. In such embodiments, the entirety of intermediate recycle stream 32 may bypass the third heat exchanger 106 during "normal" operations.

The overall composition of mixed olefin stream 12 may vary, for example, based upon upstream processing, such as in an oligomerization reactor. Due to oligomerization reactor changes over time, such as increasing reactor temperatures due to catalyst deactivation, coking/polymer build-up, or poisoning, or changes to the starting olefin mixture fed to the oligomerization, the composition of the C8+ olefinic stream 12 fed to hydrogenation reactor 100 may vary. As a result, the exotherm resulting from the hydrogenation within reactor 100 may vary. By appropriately controlling the recycle to feed volume ratio, the temperature of mixed feed stream 14 (via one or more of exchangers 102, 104, 106), hydrogen partial pressure, and other factors described above, the exotherm within reactor 100 may be appropriately controlled. Feed forward control based on compositional analysis of stream 12, feedback control based upon temperature of streams 16, and other control schemes or combinations of control schemes may be used.

Figure 2:
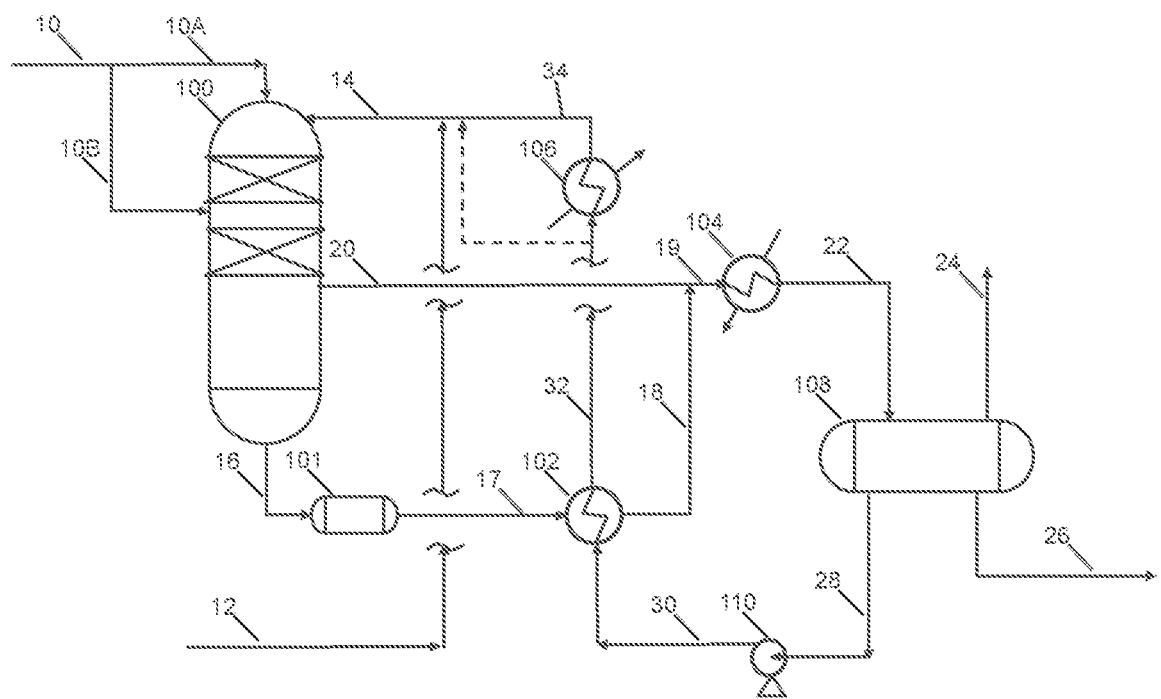
FIG. 2 is a simplified process flow diagram of a system for hydrogenation of isoolefin mixtures according to embodiments herein.

Referring now to FIG. 2, reactor 100 may be supplemented by a small, trim reactor 101, as illustrated, to provide additional isoolefin conversion, or ensure complete, or near complete, conversion. Such a trim reactor 101 may be another trickle-bed reactor, fixed bed reactor, or other reactor type which may be selected by those of ordinary skill in the art. Hydrogenated product stream 16 may be fed to the trim reactor 101 prior to the first heat exchanger 102. The additional hydrogenation reaction in the trim reactor 101 may also increase the temperature of the effluent stream 17 even further.

In one or more embodiments, where the additional trim reactor 101 is used between reactor 100 and first heat exchanger 102, the additional heat generated by the hydrogenation reaction may increase the temperature of the effluent stream 17. This heat will thus increase the temperature of intermediate recycle stream 32 coming from the first heat exchanger 102. In such embodiments, more of the recycle may bypass the third heat exchanger 106, or the third heat exchanger 106 may be taken offline entirely. Completely bypassing, or near completely bypassing, the third heat exchanger 106 may ensure that the feed temperature of mixed isoolefin stream 14 does not exceed the desired temperature.

Figure 3:
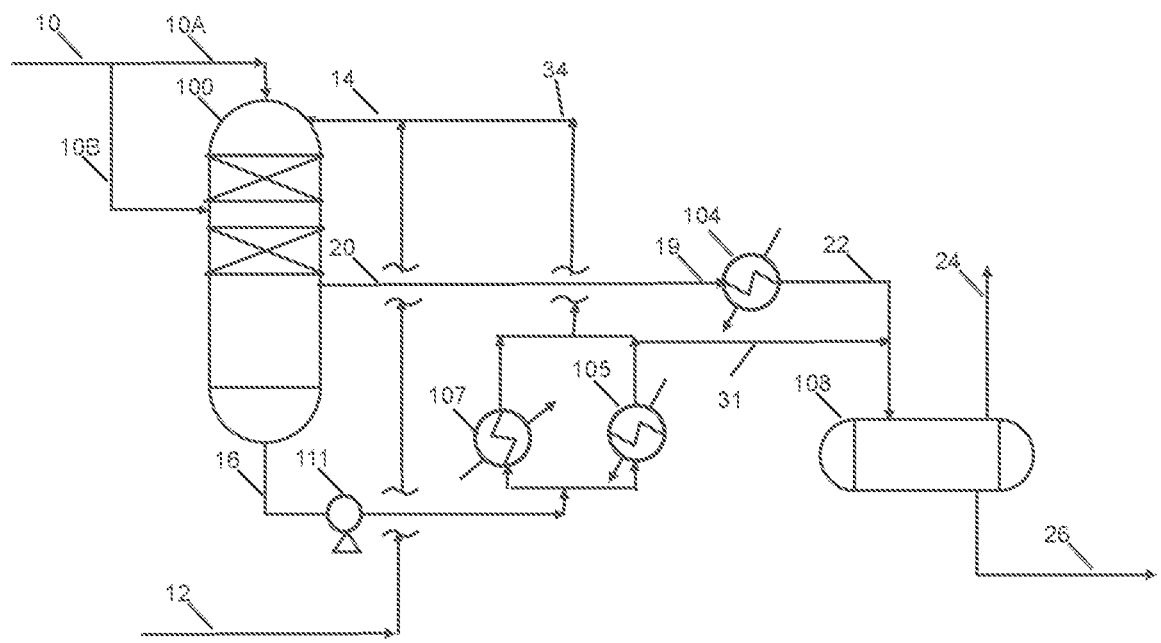
FIG. 3 is a simplified process flow diagram of a system for hydrogenation of isoolefin mixtures according to embodiments herein.

Referring now to FIG. 3, the liquid effluent 16 may be withdrawn from the bottom of reactor 100 and pressurized using pump 111. The liquid effluent may be a substantially hydrogenated product, such as above 80 wt % hydrogenated product in some embodiments, and 95 wt %+ in other embodiments, with some residual olefinic hydrocarbons. The liquid effluent 16 may be fed to heat exchangers 105 and 107 operated in parallel. Heat exchanger 107 may serve to heat the liquid effluent 16 while heat exchanger 105 may serve to cool the liquid effluent 16. By using heat exchangers 105 and 107, the temperature of the product stream 31 and heated recycle stream 34 may be controlled such that the catalyst in reactor 100 may be operated efficiently.

Accordingly, disclosed herein is a system which may flexibly produce a hydrogenated product without having to separate a mixed olefinic stream upstream of a plurality of hydrogenation units. This may be accomplished by taking a liquid phase product from the bottom of the reactor, taking a vapor phase effluent from the middle of the reactor, and pre-heating the olefinic feed through direct mixing with a relatively large volume of recycled, hydrogenated product.

Unless defined otherwise, all technical and scientific terms used have the same meaning as commonly understood by one of ordinary skill in the art to which these systems, apparatuses, methods, processes, and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A process for hydrogenation of isoolefins, the process comprising:

feeding a mixed isoolefin stream, comprising C8-C12 olefins, including isoolefins and oligomers, and C8-C12 hydrogenated hydrocarbons to a trickle-bed reactor system containing one or more beds of a hydrogenation catalyst;

feeding a hydrogen feed stream to the trickle-bed reactor system;

reacting the hydrogen feed stream and the mixed isoolefin stream in the one or more beds of hydrogenation catalyst, producing a liquid effluent comprising hydrogenated hydrocarbons and unreacted olefins and a vapor effluent comprising hydrogenated hydrocarbons, hydrogen, and unreacted olefins;

feeding the liquid effluent to a first heat exchanger, cooling the liquid effluent, and producing a cooled liquid effluent stream;

combining the vapor effluent and the cooled liquid effluent stream, producing a mixed phase effluent;

feeding the mixed phase effluent to a second heat exchanger, cooling the mixed phase effluent, and producing a partially condensed effluent;

feeding the partially condensed effluent to a drum, producing a vent stream, a hydrogenated product stream comprising greater than 95 wt % C8-C12 saturated hydrocarbons, and a hydrogenated recycle stream; and recovering the hydrogenated product stream and sending the hydrogenated product stream to one or more downstream blending systems.

2. The process of claim 1, further comprising:

pressurizing the hydrogenated recycle stream in a pump, producing a pressurized recycle stream;

feeding the pressurized recycle stream to the first heat exchanger, wherein the first heat exchanger is configured to heat the pressurized recycled stream and cool the liquid effluent, producing an intermediate recycle stream; and combining the intermediate recycle stream with a fresh isoolefin stream comprising C8-C12 olefins, including isoolefins and oligomers, producing the mixed isoolefin stream.

3. The process of claim 1, further comprising recovering the vapor effluent from a side-draw located proximate a bottom of the one or more beds of the hydrogenation catalyst.

4. The process of claim 1, further comprising feeding the hydrogen feed stream at a first hydrogen feed inlet located proximate a top of the trickle-bed reactor system, or at a second hydrogen feed inlet located intermediate a first bed of the hydrogenation catalyst and a second bed of the hydrogenation catalyst, or both.

5. The process of claim 4, wherein the feeding the hydrogen feed stream occurs at a hydrogen partial pressure of 20 to 40 barg.

6. The process of claim 4, wherein the hydrogen in the hydrogen feed stream is a fed at 1.5 to 10 times a stoichiometric amount required for the hydrogenation of the C8-C12 isoolefins and C8-C12 oligomers in the mixed isoolefin stream.

7. The process of claim 2, further comprising heating the intermediate recycle stream in a third heat exchanger prior to combining the intermediate recycle stream with the fresh isoolefin stream.

8. The process of claim 7, further comprising heating the intermediate recycle stream in the third heat exchanger to a temperature sufficient to heat the mixed isoolefin stream to a temperature in a range of 30-100° C.

9. The process of claim 1, wherein the vent stream comprises hydrogen, the process further comprising recycling a portion of the vent stream to the hydrogen feed stream.

10. The process of claim 1, wherein the mixed isoolefin stream is recovered from an upstream C4/C5 oligomerization process.

11. The process of claim 1, further comprising:

pressurizing the hydrogenated recycle stream in a pump, producing a pressurized recycle stream;

feeding the pressurized recycle stream to the first heat exchanger, wherein the first heat exchanger is configured to heat the pressurized recycled stream and cool the liquid effluent, producing an intermediate recycle stream;

heating the intermediate recycle stream in a third heat exchanger, producing a heated recycle stream; and combining the heated recycle stream with a fresh isoolefin stream comprising C8-C12 olefins, including isoolefins and oligomers, producing the mixed isoolefin stream, wherein the heated recycle stream and the fresh isoolefin stream are fed to the trickle-bed reactor at a volume ratio of 3:1 to 10:1.

* * * * *